(12) United States Patent
Krishnamachari et al.

(10) Patent No.: US 8,078,273 B2
(45) Date of Patent: Dec. 13, 2011

(54) DETECTION AND CLASSIFICATION OF NEUROMUSCULAR LATE WAVE ACTIVITY FOR THE ASSESSMENT OF NEUROMUSCULAR FUNCTION

(75) Inventors: Srivathsan Krishnamachari, Cambridge, MA (US); Xuan Kong, Acton, MA (US); Brian Tracey, Arlington, MA (US); Michael Williams, Melrose, MA (US)

(73) Assignee: Neurometrix, Inc., Waltham, MA (US)

( * ) Notice: Subject to any disclaimer, the term of this patent is extended or adjusted under 35 U.S.C. 154(b) by 695 days.

(21) Appl. No.: 11/731,271

(22) Filed: Mar. 30, 2007

(65) Prior Publication Data

US 2008/0243024 A1    Oct. 2, 2008

(51) Int. Cl.
*A61B 5/04* (2006.01)
(52) U.S. Cl. ........................................................ 600/546
(58) Field of Classification Search .................... 600/546
See application file for complete search history.

(56) References Cited

U.S. PATENT DOCUMENTS

2006/0100540 A1* 5/2006 Gozani et al. ............... 600/546
2006/0217631 A1* 9/2006 Kong et al. .................. 600/554
* cited by examiner

*Primary Examiner* — Max Hindenburg
*Assistant Examiner* — Emily Lloyd
(74) *Attorney, Agent, or Firm* — Pandiscio & Pandiscio

(57) ABSTRACT

A method for the assessment of neuromuscular function by the detection and classification of late wave activity, comprising: (i) pre-processing an ensemble of traces so as to attenuate noise, PFI and baseline disturbances; (ii) identifying time segments of late wave activity in the ensemble of traces; (iii) classifying the time segments of late wave activity into F-wave, A-wave and Repeater segments by exploiting the variable morphology of F-waves across the traces and the fixed morphology of A-waves and Repeater waves across the traces; and (iv) searching the traces in the vicinity of the F-wave trace segments on a trace-by-trace basis so as to identify the F-wave onset latency.

27 Claims, 12 Drawing Sheets

Illustration of segments in an ensemble of late wave traces showing quiet, F-wave, A-wave, and repeater segments.

Illustrates the measurement setup for a NCS and shows the path of the depolarization potential due to electrical stimulus resulting in early and late waves.

Top-level flow chart of methods in this invention.

Illustration of differential-feature and mean feature trace over an ensemble of traces.

Illustration of the steps involved in PFI attenuation.

Illustrates the sequence of steps for reducing baseline disturbance using a parametric model for the average baseline.

Illustrates the sequence of steps in correcting for uneven energy distribution over traces (same sequence of steps is used for correcting uneven energy distribution over time: energy at every time instant is calculated instead).

Illustration of the sequence of steps for differential feature calculation.

DETECTION AND CLASSIFICATION OF NEUROMUSCULAR LATE WAVE ACTIVITY FOR THE ASSESSMENT OF NEUROMUSCULAR FUNCTION

FIELD OF THE INVENTION

This invention relates to methods and apparatus for the assessment of neuromuscular function, and more particularly to methods and apparatus for the assessment of neuromuscular function by the detection and classification of late wave potentials.

BACKGROUND OF THE INVENTION

Nerve conduction studies (NCS) are performed in order to detect and evaluate focal and systemic neuropathies of the peripheral nerves and the spinal nerve roots.

Carpal Tunnel Syndrome (CTS) is a common focal neuropathy caused by the compression of the median nerve at the wrist. Symptoms of mild CTS include wrist pain, tingling and numbness, while severe CTS can result in the inability to use one's hand. Focal neuropathies typically cause degradation of nerve and muscle function at the focal location and distal to the focal location. Such degradation typically causes nerve conduction to be slowed or blocked in the focal nerve segment.

Diabetic polyneuropathy (DPN) is a systemic neuropathy primarily affecting the peripheral nerves of the lower extremities. Systemic neuropathies typically degrade nerve function over substantially the entire length of the peripheral nerve, thereby causing a slowing of nerve conduction over long segments of the nerve.

Nerves typically have different structures, depending upon their use. More particularly, there are generally three different types of nerve fibers: motor fibers, sensory fibers and autonomic fibers. The motor nerve fibers innervate muscle fibers and conduct impulses from the brain to the muscle. The sensory nerve fibers conduct impulses to the brain. Autonomic nerve fibers control the homeostatic sympathetic and parasympathetic nervous systems.

Autonomic nerve fibers have small diameters and generally cannot be effectively evaluated with NCS. However, motor nerve fibers and sensory nerve fibers can generally be effectively evaluated using NCS, thereby providing clinicians with an effective tool for the assessment of neuromuscular function.

More particularly, in an NCS evaluation of a motor nerve, the motor nerve is electrically stimulated and the motor nerve fibers are assessed by measuring the electrical response of the muscle innervated by the stimulated nerve. Correspondingly, in an NCS evaluation of a sensory nerve, the sensory nerve fibers are assessed by electrically stimulating the nerve and measuring the response of the sensory nerve fibers (i) at a fixed distance from the point of stimulation, or (ii) at an anatomical site remote from the point of stimulation.

Electrical stimulation depolarizes a short segment of the nerve (motor or sensory) at the point of stimulation. If this electrical depolarization exceeds a certain threshold, an action potential impulse is initiated. This action potential impulse propagates along the nerve, both distally and proximally, from the point of stimulation.

The aforementioned action potential impulses have different forms and characters which will hereinafter be discussed in greater detail. For the sake of convenience, these action potential impulses will be discussed in the context of motor nerves and an NCS evaluation of such motor nerves, although they also have application to sensory nerves and an NCS evaluation of such sensory nerves.

Distally-propagating nerve impulses (also known as "orthodromic" impulses) reach the muscle and depolarize the muscle fibers, typically causing a response or "twitch" in the muscle. This electrical activity of the muscle is measured as a compound muscle action potential (CMAP). The muscle responses caused by the distally-propagating impulses are typically referred to as "early waves" or M-waves. The time from the application of the stimulus to the onset (i.e., first deflection from baseline) of the response waveform is generally referred to as the "latency" of the CMAP. This latency is a measure of the conduction velocity of the fastest fibers in the nerve. The amplitude of the waveform is proportional to, and is a measure of, the number of muscle fibers that are innervated by the nerve fibers. The latency and amplitude of the CMAP are used to assess the distal segment of the nerve. A delayed latency and low amplitude are generally indicative of a neuropathy. Normally, the latency and morphology of the M-waves remain unchanged from one stimulus to the next.

Impulses propagating proximally along the axons (also known as "antidromic" impulses) reach the motor neuron cell bodies in the anterior horn of the spinal cord. In a small (and random) fraction of the neurons, the neuron depolarizes again (i.e., essentially "backfiring"), resulting in a new distally-traveling impulse (this is sometimes referred to as "back propagation"). The muscle responses due to these back-propagating impulses are generally referred to as F-waves. The F-waves travel through a longer segment of the nerve and are therefore more sensitive to systemic changes in the nerve fibers. However, unlike the aforementioned M-waves, the latency and morphology of the F-waves typically vary from one stimulus to the next, and typically comprise random features. In fact, F-waves generally have noise-like or variable features associated with them. Furthermore, due to the participation of only a small fraction of neurons in the creation of the F-waves, the amplitudes of F-waves are also much smaller than the amplitudes of M-waves. Thus, while F-waves have substantial utility in evaluating certain kinds of neuropathy, they can also be significantly more difficult to analyze than M-waves, due to their highly variable features and low amplitude.

Sometimes, a few neurons have a high probability of backfiring, and the repeated backfirings of these neurons produce features that have a similar morphology across recordings. These backfirings are frequently referred to as "Repeaters". The latency of these Repeater waves is generally similar to that of other F-waves.

In addition to the aforementioned F-waves and Repeater waves, other action potential impulses are also generated proximal to the point of stimulation but not in the motor neuron itself. More particularly, normal or pathological axonal branching may exist in some nerves. These axonal branchings can produce action potential impulses that repeat with constant latency across recordings. These recurrent action potential impulses usually occur before the onset of the F-waves, and are commonly referred to as A-waves. A-waves are typically present in a significant percentage (i.e., approximately 50% or more) of the data recordings. These low amplitude A-waves are generally fairly consistent from stimulus to stimulus.

F-waves, Repeaters and A-waves may all be generated in response to the same stimulus.

The F-waves, Repeaters and A-Waves are sometimes collectively referred to as "late waves". The fraction of the recordings in which a late wave feature is present is sometimes called the persistence of the feature. For example, A-waves have a higher persistence than Repeaters.

The recorded nerve response to a stimulus is typically called a trace. The ratio of traces in which variable F-waves exist relative to the total number of traces is sometimes referred to as the "F-wave persistence". The earliest F-wave latency occurring in all traces having F-waves is frequently referred to as the "minimum F-wave latency". Similarly, the mean F-wave latency over all traces with F-waves is frequently referred to as the "mean F-wave latency".

The minimum F-wave latency, the mean F-wave latency, the F-wave persistence, the presence of A-waves, as well as other F-wave and A-wave parameters, and also the presence of Repeaters and their parameters, are frequently used to assess the proximal segment of the nerve. The delayed latency and low persistence of F-waves, and their parameters, and the presence of A-waves, are often particularly good indicators of a neuropathy. Thus, F-wave latency is frequently of significant interest to the clinician looking to assess neuromuscular function.

The highly variable morphology and very low amplitude of F-waves make latency calculations difficult due to complicating factors such as noise, power-line frequency interference (PFI) and baseline disturbance. Any algorithm that searches an entire trace for the purposes of detecting and assigning F-wave latency will generally be prone to error, since the algorithm may erroneously identify A-waves, noise, PFI and/or baseline disturbances as F-waves. Any algorithm that could correctly limit the search for F-wave latency in a trace to a limited time segment would significantly improve the accuracy of an automated F-wave latency calculation.

SUMMARY OF THE INVENTION

The present invention provides a method and apparatus for identifying time segments in an ensemble of traces and classifying these time segments as quiet, A-wave, Repeater and/or F-wave segments. The search for F-wave latency is limited to an interval around the F-wave segments, thus enhancing the accuracy of an F-wave latency assignment. The present invention also provides the means to identify multiple F-waves in the same trace by identifying multiple F-wave segments separated by quiet segments. The A-wave segments can overlap the F-wave segments or be disjointed. The masking of an F-wave onset by an A-wave segment can also be identified, and the invention provides a novel method for assigning F-wave latency in this situation.

In accordance with the present invention, a method and apparatus are provided for detecting and classifying neuromuscular late wave activity using an automated process. In one preferred form of the invention, this is done by performing the following steps:

1. Pre-processing: An ensemble of traces are pre-processed so as to attenuate noise, power-line frequency interference (PFI) and/or baseline disturbances.

2. Segmentation: Time segments of late wave activity are identified in the ensemble of traces.

3. Segment Classification: The time segments of late wave activity are classified into F-wave, A-wave and Repeater segments by exploiting the variable morphology of F-waves across the traces and the fixed morphology of A-waves and Repeater waves across the traces.

4. Latency Assignment: The traces are searched in the vicinity of the F-wave segments on a trace-by-trace basis so as to identify the F-wave onset latency. In some cases, an A-wave segment may mask the onset of an F-wave. In this situation, an estimate of F-wave latency is determined using the ensemble of traces.

The F-wave onset latency may then be used in ways well known in the art to assess neuromuscular function.

The aforementioned steps are preferably performed using a general purpose computer provided with appropriate programming, or with a dedicated computer provided with appropriate programming, in a manner which will be apparent to those skilled in the art in view of the present disclosure.

The aforementioned Pre-processing, Segmentation, Segment Classification and Latency Assignment steps will be discussed in greater detail below.

1. Pre-processing: Electronic noise introduces variable morphology across the traces, and can therefore complicate signal analysis. Furthermore, the stimulation time is not phase-synchronized to power-line frequency interference (PFI) and, therefore, PFI has a varying morphology across the traces, which can also complicate signal analysis. In addition, the traces frequently contain baseline disturbances which are primarily due to the residual energy from the M-waves: these baseline disturbances typically have a fixed morphology. The presence of noise and PFI can result in spurious F-wave segments, while the presence of baseline disturbances can result in spurious A-wave segments. Pre-processing attenuates these contaminants. This is preferably done using the following approach:

a. Electronic noise is reduced by eliminating high frequencies (using techniques well known to those skilled in the art of low-pass filtering) on a trace-by-trace basis.

b. The amplitude and phase of the PFI components, at power-line frequency and its harmonics, are estimated using a technique well known in the art, e.g., a least squares estimation. The estimated parameters are used to model the PFI and then remove the PFI from the traces (i.e., by subtracting the modeled PFI from the traces).

c. A sample-by-sample median trace is calculated from all of the traces in the ensemble. A polynomial fit of the median trace is then used to model the baseline disturbance. In order to reduce the effect of the late waves on the polynomial fit, a fixed fraction of samples (i.e., those where the error between the median trace and the baseline disturbance model is high) are rejected, and then the polynomial fit is repeated with a reduced number of samples (and possibly with uneven spacing between the samples). The rejected samples (i.e., those with high errors) are most likely caused by late wave components in the trace, and thus their removal reduces the effect of baseline disturbances. If desired, a single polynomial fit of the median trace may be replaced by piecewise continuous polynomial fits to better represent the median trace.

In an alternate embodiment, a weighting function (e.g., a weighted least-squares function) may be constructed which emphasizes portions of the data which are believed to contain baseline disturbance but no late-wave energy. This weighting function provides an alternative means for ensuring that the data used to fit the baseline will not include late-wave energy.

In a further embodiment, the weighted function approach may be combined with the piecewise continuous polynomials approach. This can be effective for data in which the baseline disturbance has very rapid variations.

2. Segmentation: Segmentation calculates a differential feature component and a mean feature component at every time instant and thresholds them so as to identify time segments within the traces.

a. The differential feature (DF) component, which represents variability across the ensemble of traces at every sample time, is calculated. Samples corresponding to F-waves will have high values in the differential feature component while samples corresponding to A-waves will have lower values in the differential feature component. Any metric that measures variability over an indexed collection of numbers can be used in this process. In a preferred embodiment of the invention, standard deviation of the trace values is used as the measure of variability. The differential feature component is checked against a threshold and partitioned into intervals of high and low activity (i.e., to signify periods of high and low variability). In accordance with the present invention, the intervals of high DF activity are presumed to be F-wave segments.

b. The mean feature (MF) component, which represents constancy across the ensemble of traces at every sample time, is calculated. Samples corresponding to A-waves will have high values in the mean feature component while samples corresponding to F-waves will have lower values in the mean feature component. Any metric that measures constancy over an indexed collection of numbers can be used in this process. In a preferred embodiment of the invention, the average of the trace values is used as the measure of constancy. The mean feature (MF) component is checked against a threshold and partitioned into intervals of high and low activity (i.e., to signify periods of high and low constancy). In accordance with the present invention, the intervals of high MF activity have the potential to be an A-wave segment or a Repeater wave segment.

Thus, in accordance with the present invention, the ensemble of traces is divided into a plurality of time segments, based on the activity levels of the DF component and the MF component: whenever the DF component and the MF component change state (i.e., from a high activity level to a low activity level, or vice-versa), there is a time segment demarcation. Periods where both the DF component and the MF component are low indicate a quiet segment. Periods where either the DF component or the MF component are high indicate late wave activity. Furthermore, where the DF component is high, there is presumed to be F-wave activity, and where the MF component is high, there is the potential for there to be either A-wave or Repeater wave activity.

A more specific determination of the nature of the late wave activity within a specific time segment is made in the following Segment Classification step.

3. Segment Classification: The trace waveforms within a time segment having a high DF or MF activity level (i.e., a time segment reflecting late wave activity) are grouped into clusters based on a morphology similarity metric. In a preferred embodiment of the invention, the cross-correlation coefficient is used as the morphology similarity metric. An interval is classified as an A-wave segment or a Repeater wave segment if the cluster size exceeds appropriate threshold levels. High activity differential feature intervals that are not classified as an A-wave segment or a Repeater wave segment (i.e., because they do not meet the aforementioned threshold tests) are classified as F-wave segments. High activity mean feature intervals that are not classified as A-wave or Repeater wave segments (i.e., because they do not meet the aforementioned threshold tests) are discarded.

Thus, in accordance with the present invention, the time segments are classified as quiet segments, F-wave segments, or A-wave or Repeater segments, as follows. Time segments having low DF and MF activity levels are classified as a quiet segment. Time segments having high DF activity are classified as an F-wave segment. Time segments having a morphology similarity metric above a pre-determined threshold are characterized as an A-wave or Repeater segment. Time segments not otherwise classified are discarded.

4. Latency Assignment: A-waves can mask the onset of F-waves, and therefore the onset of F-waves cannot be reliably determined by traditional methods that identify the start of trace activity in individual traces after a quiet interval. However, the present invention provides a means for reliably determining the onset of F-wave activity. More particularly, in order to reduce the possibility that an earlier A-wave onset may be incorrectly characterized as the F-wave latency, the differential feature trace is used to differentiate A-waves (which have lower differential feature values) from F-waves (which have higher differential feature values). More particularly, after the F-wave segments have been identified, the algorithm for calculating F-wave latency is applied to a small interval around the identified F-wave segment for each trace. Where an A-wave overlaps with the F-wave, so that the F-wave onset is masked by an A-wave segment, the F-wave latency is established at the point at which the differential feature trace drops below a certain threshold value (i.e., the point at which only A-waves are present). This approach prevents the earlier A-wave onset from being treated as the F-wave latency, thereby improving the sensitivity of the test.

Thus, with the present invention, the DF component and the MF component are used to track the end of A-wave activity (which is characterized by low DF values and high MF values) and the start of F-wave activity (which is characterized by high DF values and low MF values), and this approach permits an accurate determination to be made of the F-wave latency.

The F-wave onset latency may then be used in ways well known in the art to assess neuromuscular function.

The aforementioned steps are preferably performed using a general purpose computer provided with appropriate programming, or with a dedicated computer provided with appropriate programming, in a manner which will be apparent to those skilled in the art in view of the present disclosure.

In one preferred form of the present invention, there is provided a method for the assessment of neuromuscular function by the detection and classification of late wave activity, comprising:

(i) pre-processing an ensemble of traces so as to attenuate at least one of noise, PFI and baseline disturbances;

(ii) identifying time segments of late wave activity in the ensemble of traces;

(iii) classifying the time segments of late wave activity into F-wave, A-wave and Repeater segments by exploiting the variable morphology of F-waves across the traces and the fixed morphology of A-waves and Repeater waves across the traces; and (iv) searching the traces in the vicinity of the F-wave segments on a trace-by-trace basis so as to identify the F-wave onset latency.

In another form of the present invention, there is provided a method for the assessment of neuromuscular function by the detection and classification of late wave activity, comprising:

identifying time segments in the ensemble of traces;

classifying the time segments as quiet, A-wave, Repeater and/or F-wave segments; and determining F-wave latency by (i) identifying any masking of an F-wave by an A-wave segment, (ii) where masking occurs, using the differential feature component to differentiate the A-wave from the F-wave, and (iii) establishing the F-wave latency from the point at which only the A-wave is present.

In another form of the present invention, there is provided a method for the assessment of neuromuscular function by the detection and classification of late wave activity, comprising:

determining a differential feature component and a mean feature component across an ensemble of traces;

identifying time segments in the ensemble of traces;

classifying the time segments as quiet, A-wave, Repeater and/or F-wave segments; and determining F-wave latency by using the start of the F-wave segment to identify the onset of the F-wave.

In another form of the present invention, there is provided apparatus for the assessment of neuromuscular function by the detection and classification of late wave activity, comprising:

(i) apparatus for pre-processing an ensemble of traces so as to attenuate at least one of noise, PFI and baseline disturbances;

(ii) apparatus for identifying time segments of late wave activity in the ensemble of traces;

(iii) apparatus for classifying the time segments of late wave activity into F-wave, A-wave and Repeater wave segments by exploiting the variable morphology of F-waves across the traces and the fixed morphology of A-waves and Repeater waves across the traces; and (iv) apparatus for searching the traces in the vicinity of the F-wave trace segments on a trace-by-trace basis so as to identify the F-wave onset latency.

In another form of the present invention, there is provided apparatus for the assessment of neuromuscular function by the detection and classification of late wave activity, comprising:

apparatus for identifying time segments in an ensemble of traces;

apparatus for classifying the time segments as quiet, A-wave, Repeater and/or F-wave segments; and apparatus for determining F-wave latency by (i) identifying any masking of an F-wave by an A-wave segment, (ii) where masking occurs, using the differential feature component to differentiate the A-wave from the F-wave and (iii) establishing the F-wave latency from the point at which only the A-wave is present.

In another form of the present invention, there is provided apparatus for the assessment of neuromuscular function by the detection and classification of late wave activity, comprising:

apparatus for determining a differential feature component and a mean feature component across an ensemble of traces; identifying time segments in the ensemble of traces;

apparatus for classifying the time segments as quiet, A-wave, Repeater and/or F-wave segments; and apparatus for determining F-wave latency by using the start of the F-wave segment to identify the onset of the F-wave.

The invention will be understood further upon consideration of the following description, drawings and claims.

DETAILED DESCRIPTION OF THE PREFERRED EMBODIMENTS

In a nerve conduction study (NCS), the nerve is electrically stimulated so as to depolarize a short segment of the nerve at the point of stimulation. If the depolarization is of sufficient magnitude, a compound action potential is induced in some number of the axons within the nerve. This compound action potential propagates distally and proximally from the point of stimulation. By evaluating the propagation of these compound action potentials through the nerve, the assessment of neurological function can be made.

Figure 1:
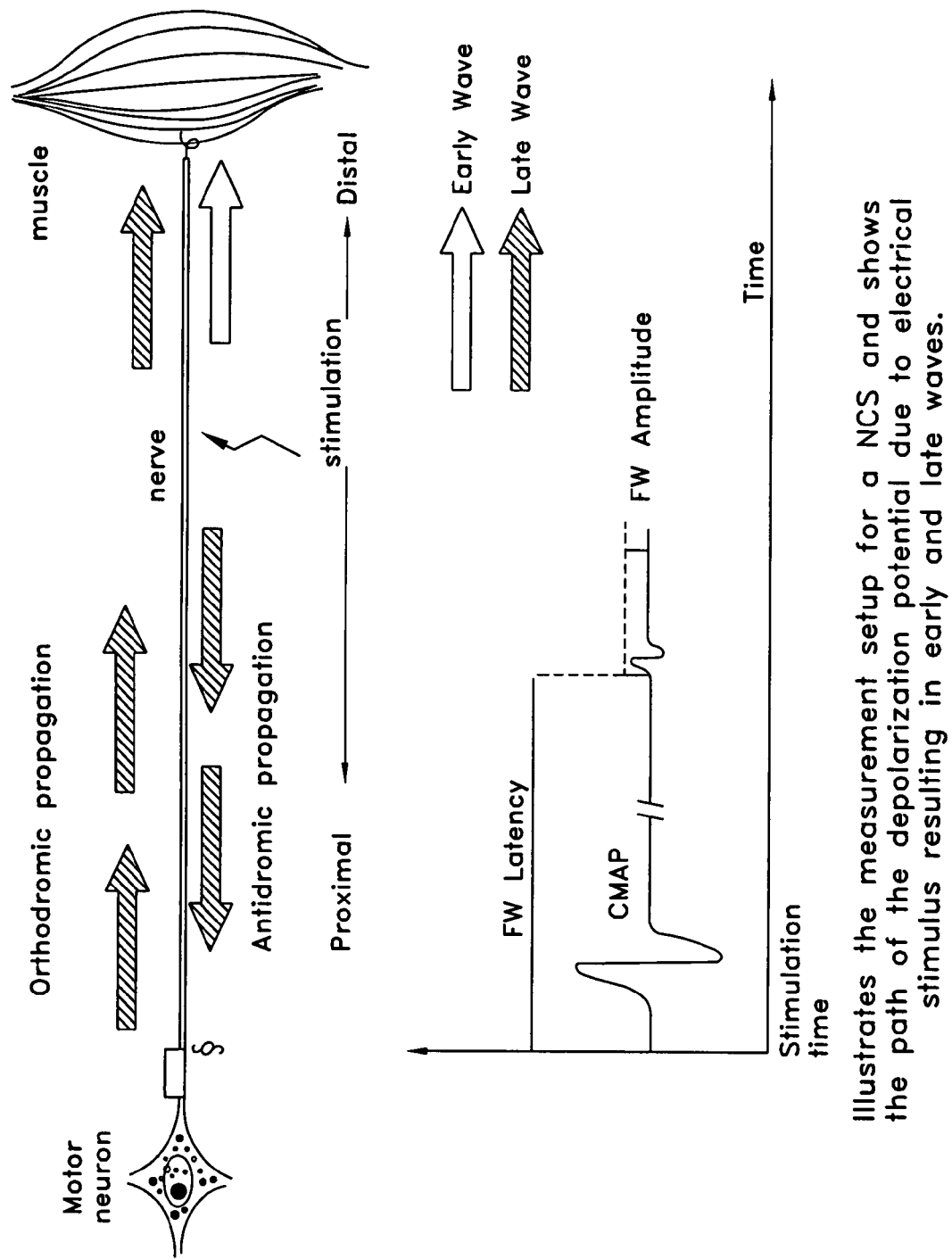
FIG. 1 illustrates the measurement setup for an NCS measurement of a motor nerve, and shows the path of impulse propagation due to the application of an electrical stimulus, resulting in M-waves and late waves.

See, for example, FIG. 1, which illustrates two compound action potentials (i.e., CMAP and F-wave compound action potentials) in the context of an NCS measurement of a motor nerve.

For the sake of convenience, the compound action potentials may hereinafter frequently be discussed in the context of an NCS measurement of a motor nerve. However, it should be appreciated that the discussion of compound action potentials also has application to sensory nerves and the NCS evaluation of sensory nerves.

The distally-propagating compound action potential ("orthodromic") reaches the muscle and activates neurotransmitter releases at the neuromuscular junction, which then activate muscle fibers and cause muscle contraction. The electrical activity of the muscle is measured as the compound muscle action potential (CMAP). The muscle responses induced by distally-propagating compound action potentials are frequently called M-waves. Normally, the latency and morphology of M-waves remain unchanged from one stimulus to the next. M-waves can be an important indicator of neuromuscular function in the distal portion of the nerve, and hence are frequently of significant interest to a clinician looking to assess neuromuscular function.

The proximally-propagating compound action potential ("antidromic") reaches the motor neuron cell bodies. In a small and random fraction of the neurons, the neurons "backfire", resulting in a new, distally-traveling compound action potential ("back propagation"). The muscle responses due to the back-propagating compound action potential are called F-waves. Unlike M-waves, the latency and morphology of F-waves typically vary significantly from one stimulus to the next. Due to the participation of only a small fraction of the neurons, the amplitude of F-waves are also much smaller than that of M-waves. F-waves can be an important indicator of neuromuscular function along the full length of the nerve, and hence are frequently of significant interest to a clinician looking to assess neuromuscular function.

Sometimes, a few neurons have a high probability of backfiring, and the repeated backfiring of these neurons produces features in late waves that have a similar morphology across multiple recordings. These specific F-waves are sometimes called Repeaters. The latency of Repeater waves is similar to that of F-waves. Repeater waves can also be an important indicator of neuromuscular function along the full length of the nerve, and hence are frequently of significant interest to a clinician looking to assess neuromuscular function.

Normal or pathological axonal branching may exist in some nerves. The axonal branching can produce action potential impulses that repeat with constant latency across multiple recordings. These recurrent action potential impulses usually occur before the onset of the F-waves, and are commonly referred to as A-waves. A-waves are typically present in a significant percentage (e.g., approximately 50%) of all traces. A-waves can also be an important indicator of neuromuscular function along the full length of the nerve, and hence are frequently of significant interest to a clinician looking to assess neuromuscular function.

The aforementioned F-waves, Repeaters and A-Waves are frequently collectively referred to as late waves. The fraction of the recordings in which a late wave feature is present is called the persistence of the feature. A-waves have a higher persistence than Repeaters.

The highly variable morphology, and very low amplitude, of F-waves make F-wave latency calculations difficult due to complicating factors such as noise, power-line frequency interference (PFI) and baseline disturbances. Any algorithm that searches an entire trace to detect and identify F-wave latency will be prone to error, since it may erroneously identify A-waves, noise, PFI and/or baseline disturbances as F-waves. Thus, a new and improved algorithm that can correctly limit the search for F-wave latency in a trace to a limited time segment can significantly improve the accuracy of F-wave latency detection and significantly improve the correct identification of other late wave components.

Figure 2:
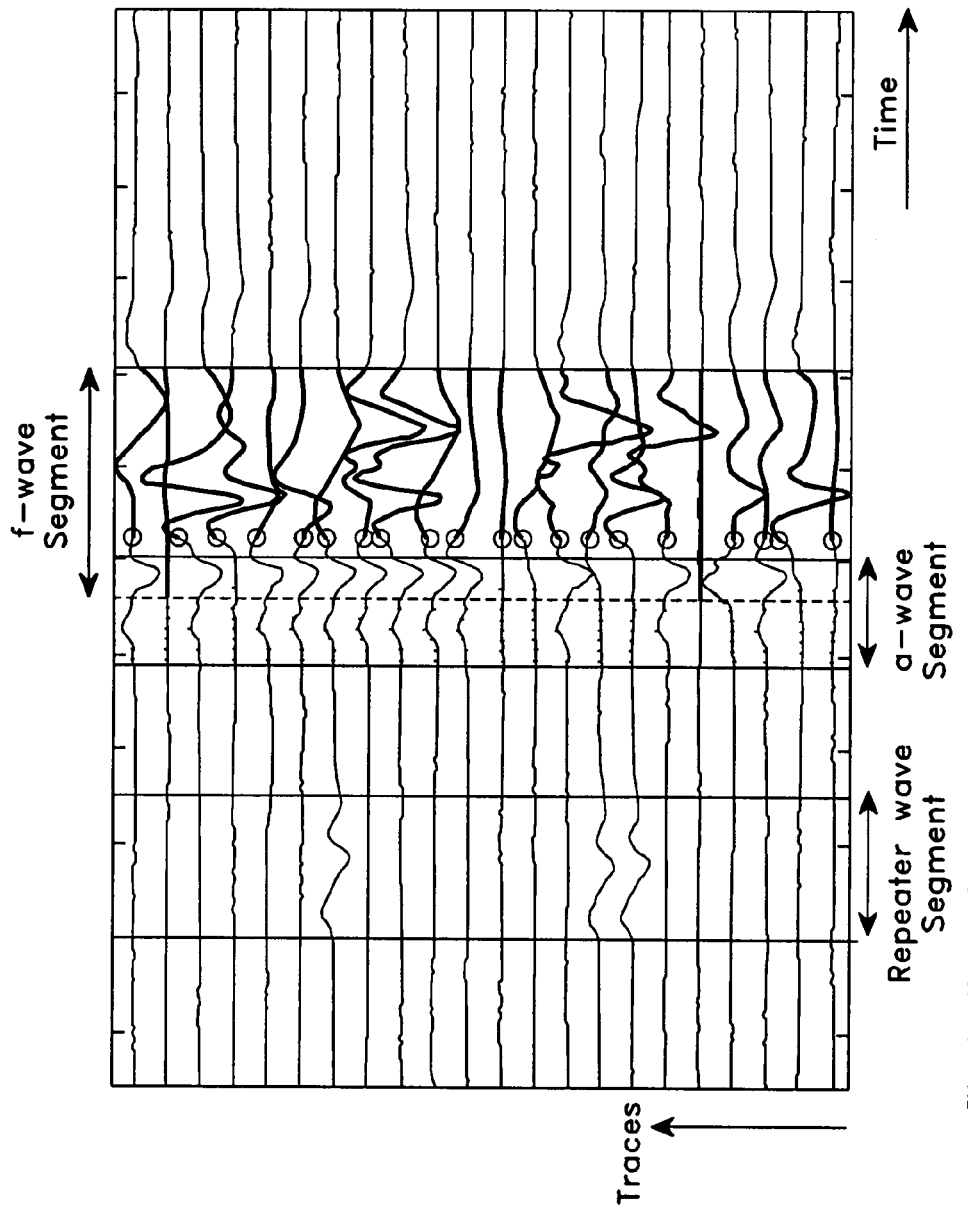
FIG. 2 illustrates segments in an ensemble of late wave traces showing quiet, F-wave, A-wave and Repeater wave segments (but not necessarily in that order)

The present invention provides a method and apparatus to identify time segments in an ensemble of traces and to classify these time segments as quiet segments, A-wave segments, Repeater segments or F-wave segments, as illustrated in FIG. 2. In accordance with the present invention, the search for F-wave latency is limited to an interval around the F-wave segments, thus enhancing the accuracy of F-wave latency assignment.

The present invention also provide a means for identifying multiple F-waves in the same trace by identifying multiple F-wave segments separated by quiet segments.

The A-wave segments can overlap the F-wave segments or be disjointed. In accordance with the present invention, the masking of F-wave onset by A-wave segments can also be identified, and the invention provides a novel approach for assigning F-wave latency in this situation.

Figure 3:
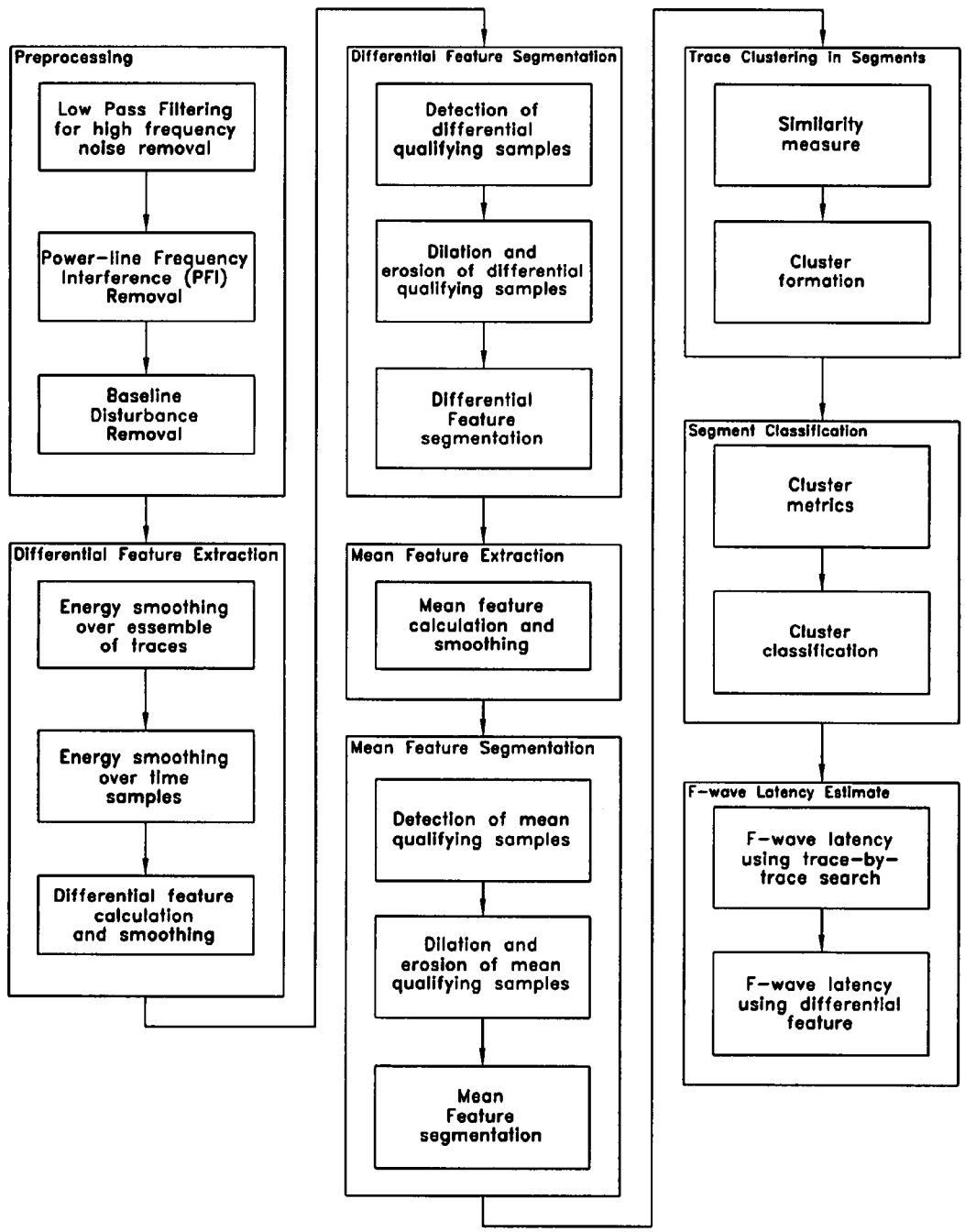
FIG. 3 illustrates, in the form of a top-level flow chart, the preferred methodologies of the present invention.

The methodology of the preferred embodiment of the invention is illustrated in FIG. 3.

1. Pre-Processing

1a. Low-Pass Filtering

Figure 11:
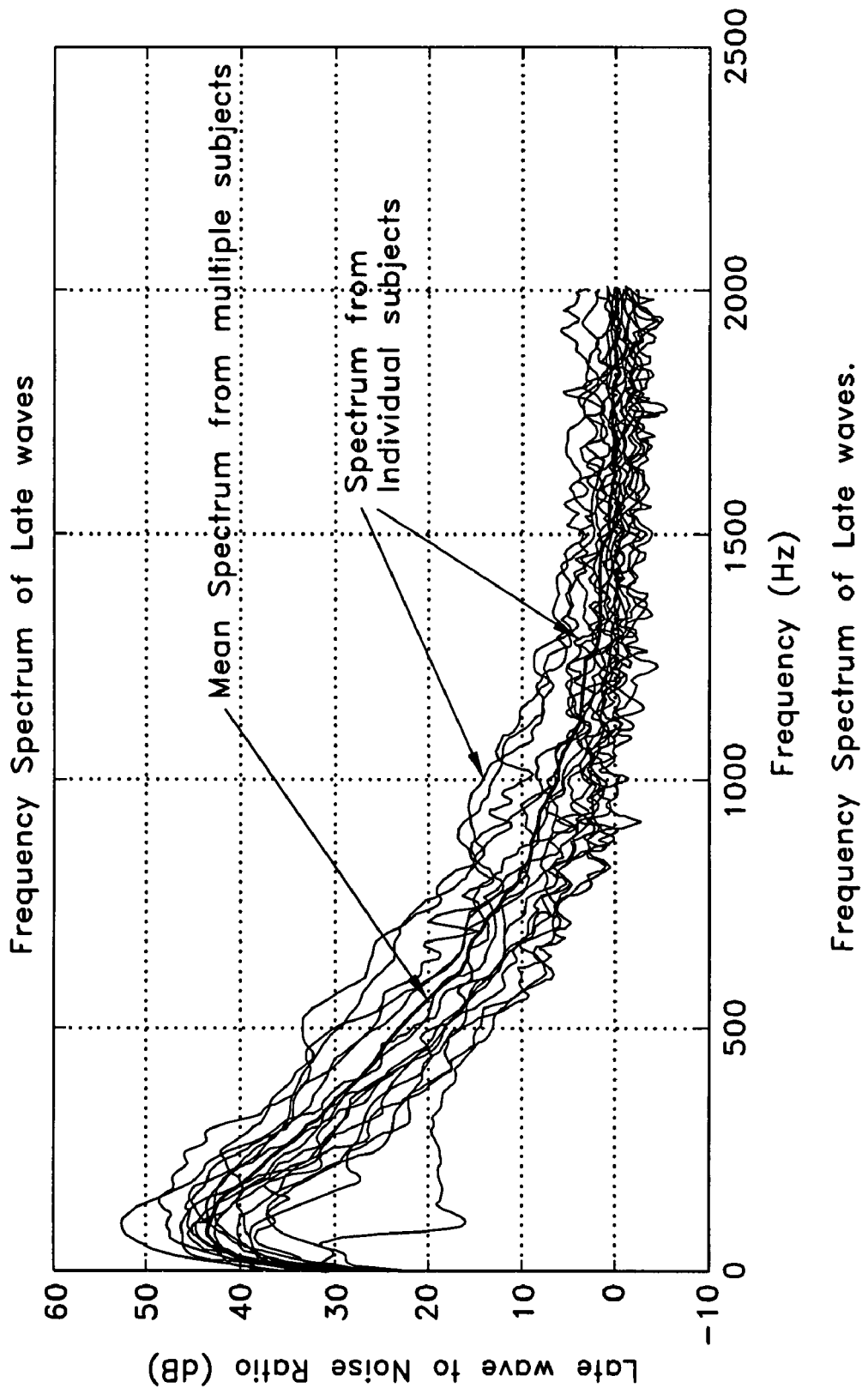
FIG. 11 illustrates the frequency spectrum of late waves.

Late waves have significant energy in the frequency range of 30-800 Hz, as illustrated in FIG. 11. In order to ensure high resolution in the time domain when determining the F-wave latency, the measured analog trace signals (after appropriate anti-alias filtering) are sampled at rates in excess of 4000 samples/s. In order to remove noise in the frequency range of over 800 Hz, the sampled trace is digitally low-pass filtered, preferably using a linear phase filter. Such linear phase filters are well known in the art, e.g., they may be FIR filters or the Bessel IIR filter. These filters are designed to have a linear phase response and they introduce a constant delay at all frequencies. The constant time delay introduced by these filters is corrected by appropriately time-shifting the output of the filter. This filtering improves the signal-to-noise ratio by eliminating high frequency noise without distorting the late wave morphology. High frequency noise is highly variable over traces and might result in the erroneous detection of spurious F-wave segments.

1b. Power-Line Frequency Interference (PFI) Removal

The PFI frequency spectrum overlaps the frequency content of the late waves. Therefore, using any linear band-stop filter with non-zero bandwidth to block PFI will affect the morphology of the F-waves. In order to avoid this problem, the phase and amplitude of the PFI fundamental frequency, and its harmonics, are estimated from the trace and used to build a model of the PFI. The modeled PFI is then subtracted from the trace in order to compensate for PFI effects. PFI removal is preferably done in four steps on a trace-by-trace basis. These four steps are illustrated in FIG. 5.

Figure 5:
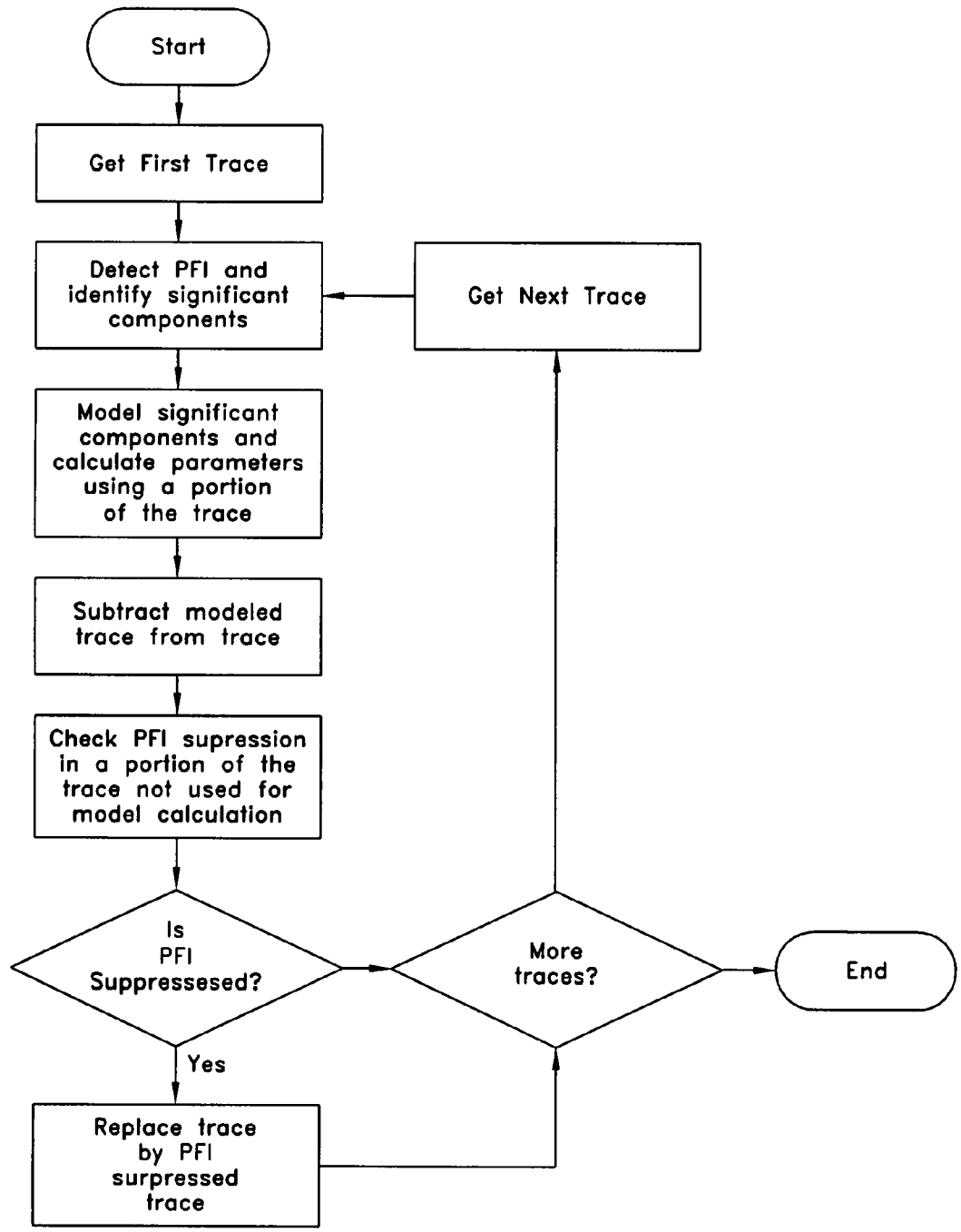
FIG. 5 illustrates the preferred steps involved in PFI attenuation.

In the first step shown in FIG. 5, the trace is checked for the presence of the PFI fundamental frequency and its harmonics. This check calculates the power in the frequency spectrum (preferably calculated using Fast Fourier transform techniques) at the fundamental frequency and its harmonics. The frequency components with significant energy (e.g., 2 uV or more in the preferred embodiments) are used to model the PFI.

In the second step shown in FIG. 5, the model parameters are estimated. The model for PFI, when the fundamental and second harmonic have significant energy, is $$C_0 + A_1 \cos(2\pi f_0 t) + B_1 \sin(2\pi f_0 t) + A_2 \cos(2\pi 2 f_0 t) + B_2 \sin(2\pi 2 f_0 t).$$

$y(n)$, $n=1 \ldots N$ is the part of the trace from which the PFI parameters are estimated. This selected part of the trace should not contain any early or late wave signals. Accordingly, in the preferred embodiment of the invention, this part of the trace is acquired prior to the application of the electrical stimulus, and its time relationship to the post-stimulus signal is known. $f_0$ is the fundamental frequency of PFI, and $\Delta t$ is the sampling time. $C_0, A_1, A_2, B_1, B_2$ are the model parameters to be estimated by solving the system of equations:

$$\begin{bmatrix} y(0) \\ y(1) \\ y(2) \\ \vdots \\ y(N) \end{bmatrix} = \begin{bmatrix} 1 & 1 & 1 & 1 & 1 \\ 1 & \cos(2\pi f_0 \Delta t) & \sin(2\pi f_0 \Delta t) & \cos(2\pi 2 f_0 \Delta t) & \sin(2\pi 2 f_0 \Delta t) \\ 1 & \cos(2\pi f_0 2\Delta t) & \sin(2\pi f_0 2\Delta t) & \cos(2\pi 2 f_0 2\Delta t) & \sin(2\pi 2 f_0 2\Delta t) \\ 1 & \vdots & \vdots & \vdots & \vdots \\ 1 & \cos(2\pi f_0 N\Delta t) & \sin(2\pi f_0 N\Delta t) & \cos(2\pi 2 f_0 N\Delta t) & \sin(2\pi 2 f_0 N\Delta t) \end{bmatrix} \begin{bmatrix} C_0 \\ A_1 \\ B_1 \\ A_2 \\ B_2 \end{bmatrix}$$

This system of equations is preferably solved using least square techniques. The constructed model is subtracted from the trace to attenuate the PFI.

In the third step shown in FIG. 5, the estimated model is extrapolated for all time samples in the trace. The extrapolated PFI model is subtracted from the trace so as to obtain the PFI-corrected trace.

In the last step shown in FIG. 5, PFI components are estimated from a section of the uncorrected trace that is not used for PFI parameter estimation. A similar estimation is made from the PFI-corrected trace. If the PFI components are not attenuated in the corrected trace, it is an indication of inaccurate PFI correction and, therefore, the PFI-corrected trace is discarded and no PFI correction is performed for this trace. Otherwise, the PFI-corrected trace is used in subsequent processing steps.

In order to avoid late waves from affecting the estimation, the trace can include a signal measured before the application of a stimulus. This pre-stimulus signal in the trace is used to estimate PFI interference. Any interval of the trace that can be guaranteed to be free of early and late waves, and with a known time relationship to the stimulus, can be used for this purpose.

1c. Baseline Disturbance Removal

Figure 6:
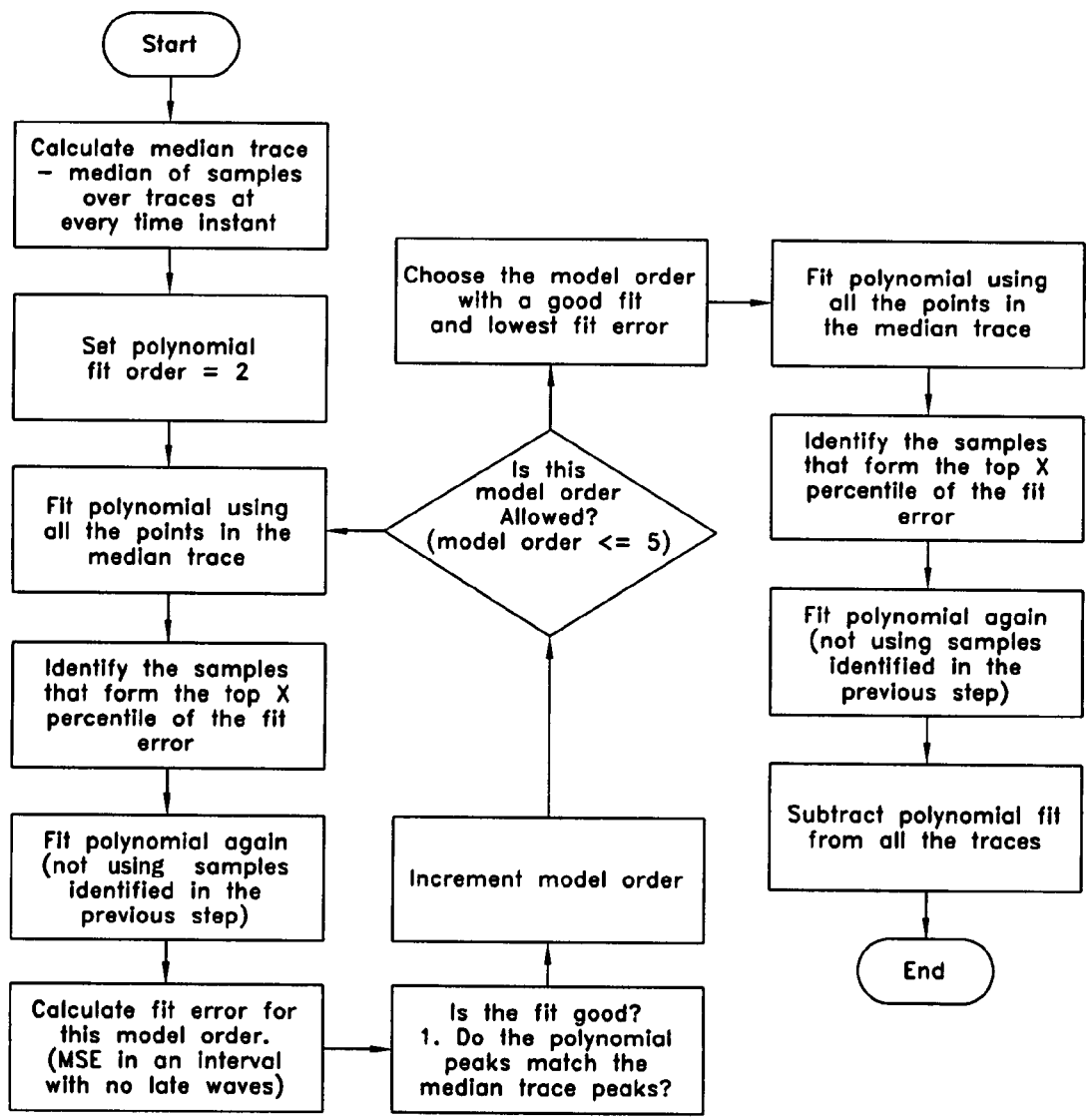
FIG. 6 illustrates the preferred steps involved in reducing baseline disturbance using a parametric model to establish the average baseline model.

Baseline disturbance is commonly due to the lingering residual energy of the M-waves. The M-waves have significantly higher amplitude than late waves and, therefore, can cause severe baseline disturbance during the late waves. In some cases, a baseline disturbance may be due to the frequency response of the data acquisition hardware. The M-waves have a fixed morphology and therefore the baseline disturbance is stable across the traces. FIG. 6 illustrates the preferred methodology for reducing baseline disturbance.

The stable nature of the baseline disturbance can be exploited to get a good estimate of the disturbance by calculating a sample-wise averaging estimate. In a preferred embodiment of the present invention, the median of all trace values at every time instant is used to estimate the disturbance at that time instant. This estimate is called the average baseline estimate (ABE).

The ABE might include some late wave features, especially from the A-waves and Repeater waves. Parametric modeling of the ABE is performed to remove late wave features from the ABE. A polynomial fit model (PFM) is preferably used as the parametric model in the preferred embodiment of the invention. In other embodiments, inverse filter and deconvolution models, reversing the effects of the hardware frequency response, can also be used. Low order polynomials are used to prevent the polynomial fit from introducing artificial late wave features.

The peaks in the polynomial fit are checked so that the polynomial fit does not introduce any new feature that would create spurious A-waves. The spurious peak check includes checking the distance between peaks in the PFM and matching the peaks in the PFM to the peaks in ABE. If the peaks in the polynomial fit are too close to each other (e.g., 10 ms in the preferred embodiment), or if the peaks in the PFM are not present in the ABE, then the PFM of that order is rejected. The mean square error between the ABE and PFM in an interval guaranteed to be free of late waves (this can be determined from normative F-wave latencies) is calculated. In the preferred embodiment, PFM's with polynomial orders between 2 and 5 are evaluated. The lowest order PFM that best fits the ABE (e.g., the lowest mean square error) and passes the spurious peak check is used as the final baseline estimate.

The PFM of a particular order of the ABE is calculated using an iterative process that preferably has three steps. In the first step, a PFM is calculated using all the time samples in the trace. The polynomial fit is done using least square estimation techniques. The error between PFM and ABE is calculated. In the second step, a fixed percentile (e.g., the 25$^{th}$ percentile in the preferred embodiment) of the time samples is excluded from the next step, i.e., those time samples in which the error between PFM and ABE is high. These excluded samples are most likely to have late-wave features. In the last step, the PFM of the same order is recalculated using the retained (i.e., included) samples from the previous step. The retained samples may have uneven spacing between them.

The best PFM is then subtracted from every trace in order to compensate for baseline disturbances in the ensemble of traces.

There may be some baseline disturbances that may not be constant over all traces. These baseline disturbances can be attenuated by using a trace-by-trace PFM instead of a PFM of the ABE. However, this should be done with caution, as there is an increased chance of introducing spurious F-wave segments. The difference in the PFM for each trace may produce a varying morphology across traces that may mimic F-waves.

In some cases, the baseline disturbance may vary rapidly, so that using a single polynomial to model the entire baseline disturbance does not produce a good (i.e., adequate) fit. Therefore, an alternate embodiment has been developed which uses piecewise continuous polynomial fits. In this alternate embodiment, the ensemble of late wave traces is first analyzed to determine an acceptable "break-point", or time sample, that marks the transition point between the first and second regions of data. Next, a polynomial is fit to the data in each region using a technique known to those skilled in the art as weighted least-squares (or using another polynomial-fitting technique of the sort which will be apparent to those skilled in the art in view of the present disclosure). The polynomials selected for each region may be, and generally are, different from the polynomials selected for other regions. Finally, the regional fits are joined together. While the embodiment is discussed in terms of two polynomial sections, it will be clear to those skilled in the art that the method can be extended to an arbitrary number of polynomial segments.

More particularly, as a first step, the sample-by-sample standard deviation across traces is used to calculate a threshold which separates the data into high-activity and low-activity regions. This threshold is found by sorting the standard deviation values in ascending order and looking for points at which the standard deviation begins to increase rapidly. The standard deviation at which this transition occurs provides a threshold for separating high and low activity. In a preferred embodiment, the threshold estimate is constrained to lie between the median and 75th percentile of all standard deviation values.

The median waveform is low-pass filtered and analyzed to find any peaks in the early part of the median trace (in this embodiment, peaks in the first third of the trace are allowed). The earliest such peak is a candidate "break-point". If the break point is in a quiet region, it is accepted as the break-point as it presumably represents an inflection point of the baseline disturbance. If it is in a high-activity region, it is rejected as it may represent late-wave activity. In this case, the latest time sample which is prior to the peak, and is in a quiet region, is used as the break-point. If no valid break-points are identified, a single polynomial will be used to fit the entire baseline.

In the second step, a widely-used technique known as weighted least-squares is used to estimate the polynomial coefficients. This technique requires as input a vector of weights, equal in length to the data, which indicates how strongly each data sample should influence the least-squares solution. In one embodiment, the weight at each time sample is equal to 1 divided by the variance across traces at that sample. This de-weights noisy regions, which are less likely to represent baseline disturbance. In a preferred embodiment, the weights are additionally modified by setting the weights in high-activity regions to a very low value. Weights in very quiet regions are also limited so they do not increase beyond a user-defined value. Weights calculated in this manner are sometimes referred to herein as "ensemble weights".

The polynomial fits for the two regions of the trace are next calculated. For the first portion of the data, a weighting vector is constructed whose values are equal to the ensemble weights for samples before the break-point, but are strongly de-weighted (or set to zero) for samples after the break-point.

A polynomial fit is then calculated. This fit should match the data well before the break-point, but is not expected to be accurate after the break-point. For the second portion of data, a weighting vector is calculated whose values are very small (or zero) before the break-point, but are equal to the ensemble weights for time samples after the break-point. The fit calculated using these weights is expected to match the data well at times later than the break-point. The second fit is constrained so its value is continuous with the first fit at the break-point.

Finally, an overall polynomial fit is constructed. This overall fit is equal to the first polynomial fit for times before the break-point, and is equal to the second polynomial fit at later times. A moving average filter may be used to smooth the overall fit.

2. Differential Feature Extraction

Figure 4:
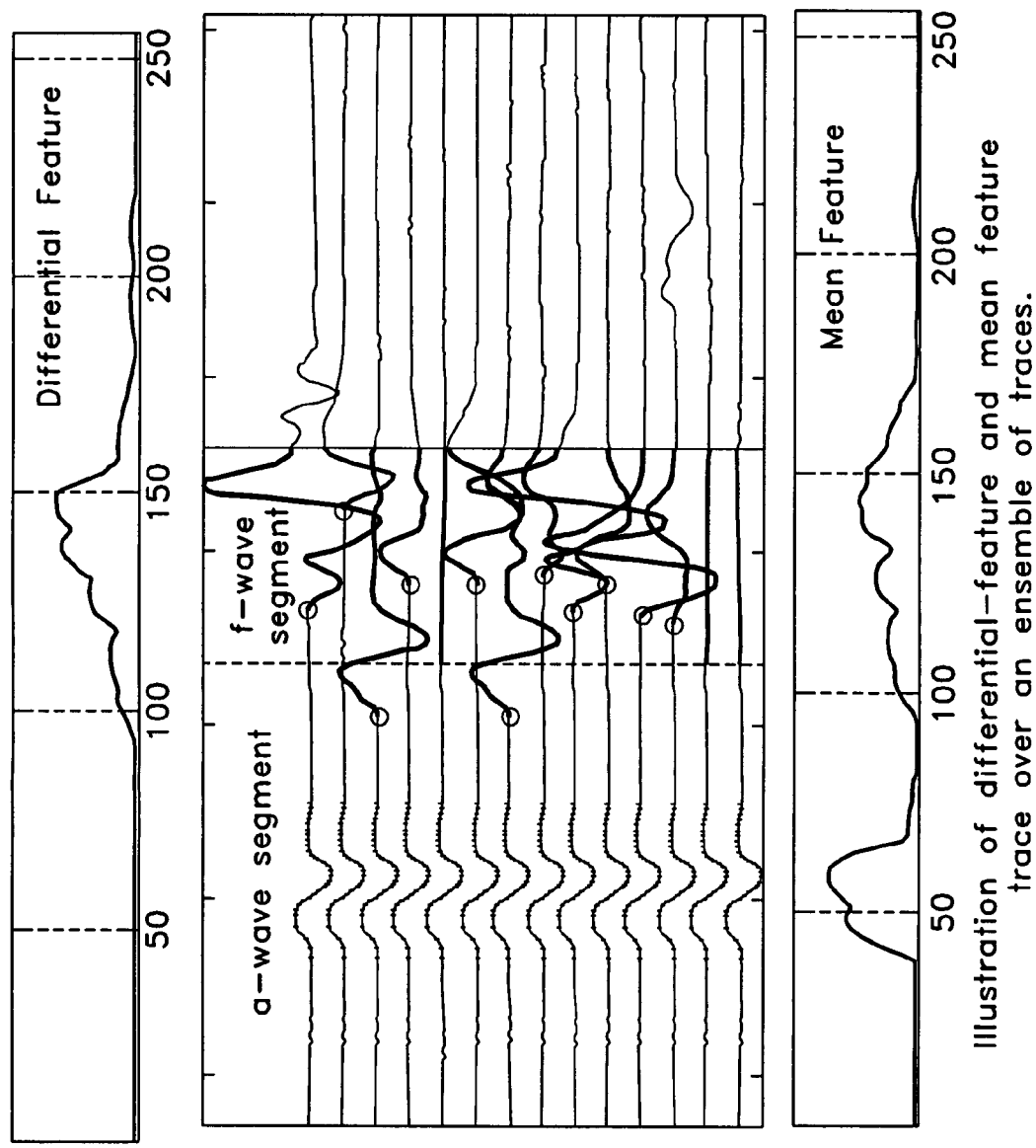
FIG. 4 illustrates an ensemble of traces, and the differential feature component and the mean feature component derived from those traces.

The differential feature (DF) component represents variability across the ensemble of traces at every sample time. Samples corresponding to F-waves will have a high DF value, while samples corresponding to A-waves will have a lower DF value. This is illustrated in FIG. 4. Any metric that measures variability over an indexed collection of numbers can be used in this method. In a preferred embodiment of the invention, standard deviation of the trace values is used as the measure of variability. The DF component is smoothed so as to eliminate narrow breaks in the DF component and to discard narrow intervals of activity. The DF component is split into intervals of high and low activity. In accordance with the present invention, the intervals of high DF activity are considered to be late wave segments.

2a. Energy Smoothing Over Ensemble of Traces

Figure 7:
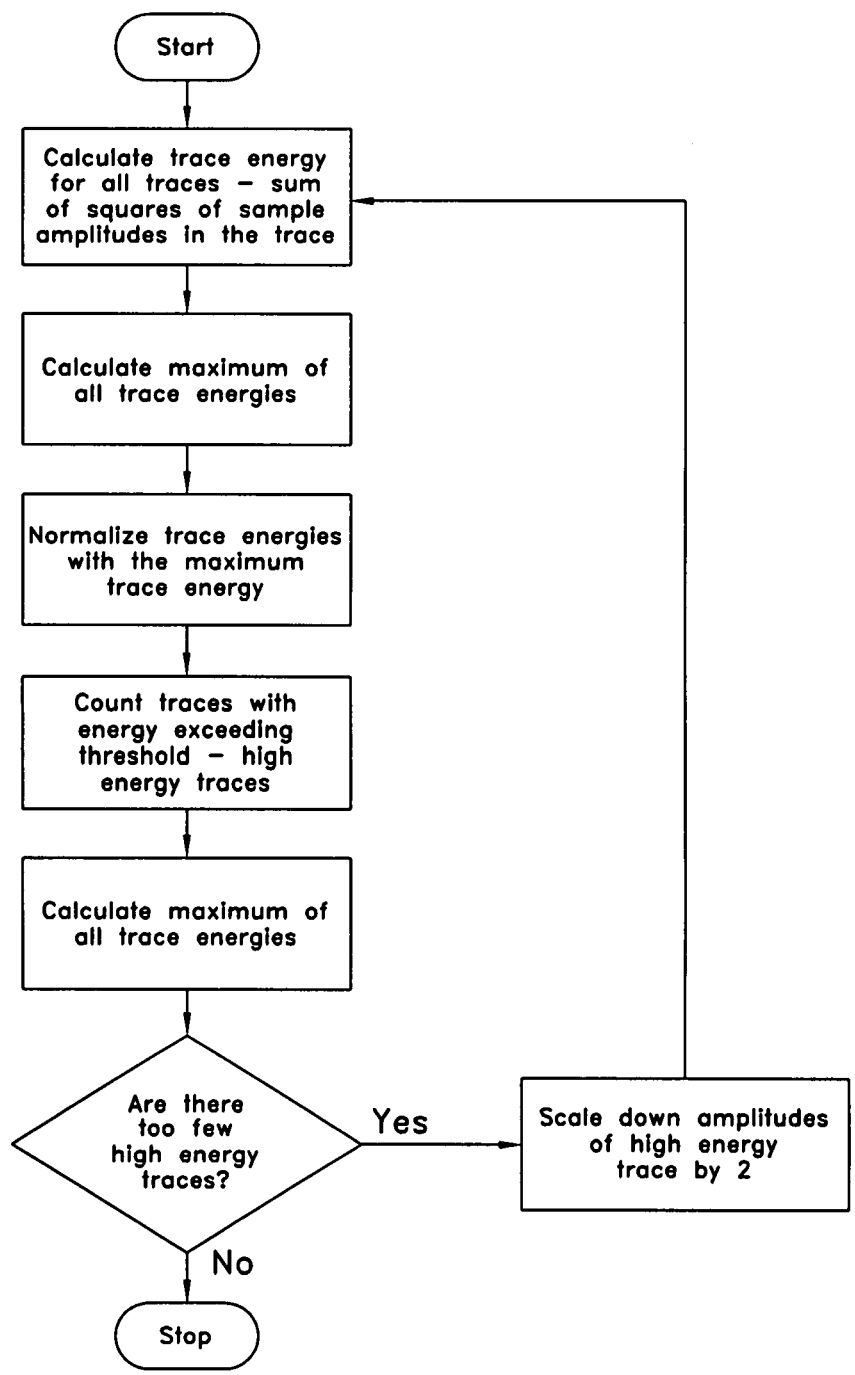
FIG. 7 illustrates the preferred steps involved in correcting for uneven energy distribution over traces.

In some cases, the late wave energy in a small fraction of the traces might be many times larger than in the other traces. These high-energy traces might dominate the DF component, and smaller F-waves in the other traces in other time intervals might not be detected, since late wave segments are identified in the present invention by the presence of high DF values. Therefore, the energy of this small fraction of high-energy traces is reduced in order to improve the visibility of low energy F-waves in the DF component. This energy scaling is preferably done using the following methodology, which is illustrated in FIG. 7.

1. Calculate the trace energy in every trace by summing the square of all the sample amplitudes in that trace.
2. Calculate the maximum trace energy and use it to normalize all the trace energies to be between 0 and 1.
3. Count the number of traces with normalized energy greater than a certain threshold. A preferred embodiment of the invention uses a threshold value of 0.2. These are considered to be the high-energy traces.
4. If the high-energy trace count is less than a pre-determined threshold (this count threshold can be a combination of a fixed number and a fraction of the total number of traces in the ensemble), it indicates uneven energy distribution across the traces.
5. If uneven energy distribution is detected, the high-energy traces are scaled by a factor of 2.
6. The foregoing steps can be repeated as needed until uneven energy distribution is no longer detected. In the preferred embodiment of the present invention, the foregoing steps are typically repeated twice.

2b. Energy Smoothing Over Time Samples

In some cases, the late wave energy in a small time interval might be many times larger than in other time instants. These high-energy intervals may dominate the DF component, and smaller F-waves in other time intervals might not be detected, since late wave segments are identified in the present invention by the presence of high DF values. Therefore, the energy of this small fraction of high-energy intervals is reduced in order to improve the visibility of low energy F-waves in the DF component. This energy scaling is preferably done using the following methodology, which is similar to that shown in FIG. 7.

1. Calculate the signal energy at every time instant by summing the square of the sample amplitudes from all of the traces at that time instant.
2. Calculate the maximum time energy and use it to normalize all of the time energies so that they are between 0 and 1.
3. Count the number of time instants with a normalized energy greater than a certain threshold. The preferred embodiment uses a threshold value of 0.2. These are considered to be the high-energy time instants.
4. If the high-energy time instant count is less than a certain threshold (this count threshold can be a combination of a fixed number and a fraction of the total number of samples in the traces), it indicates uneven energy distribution across time.
5. If uneven energy distribution is detected, the samples at the high-energy time instants are scaled by a factor of 2.
6. The foregoing steps can be repeated as needed until uneven energy distribution is no longer detected. In the preferred embodiment of the present invention, the steps are typically not repeated.

2c. Differential Feature Calculation and Smoothing

Figure 8:
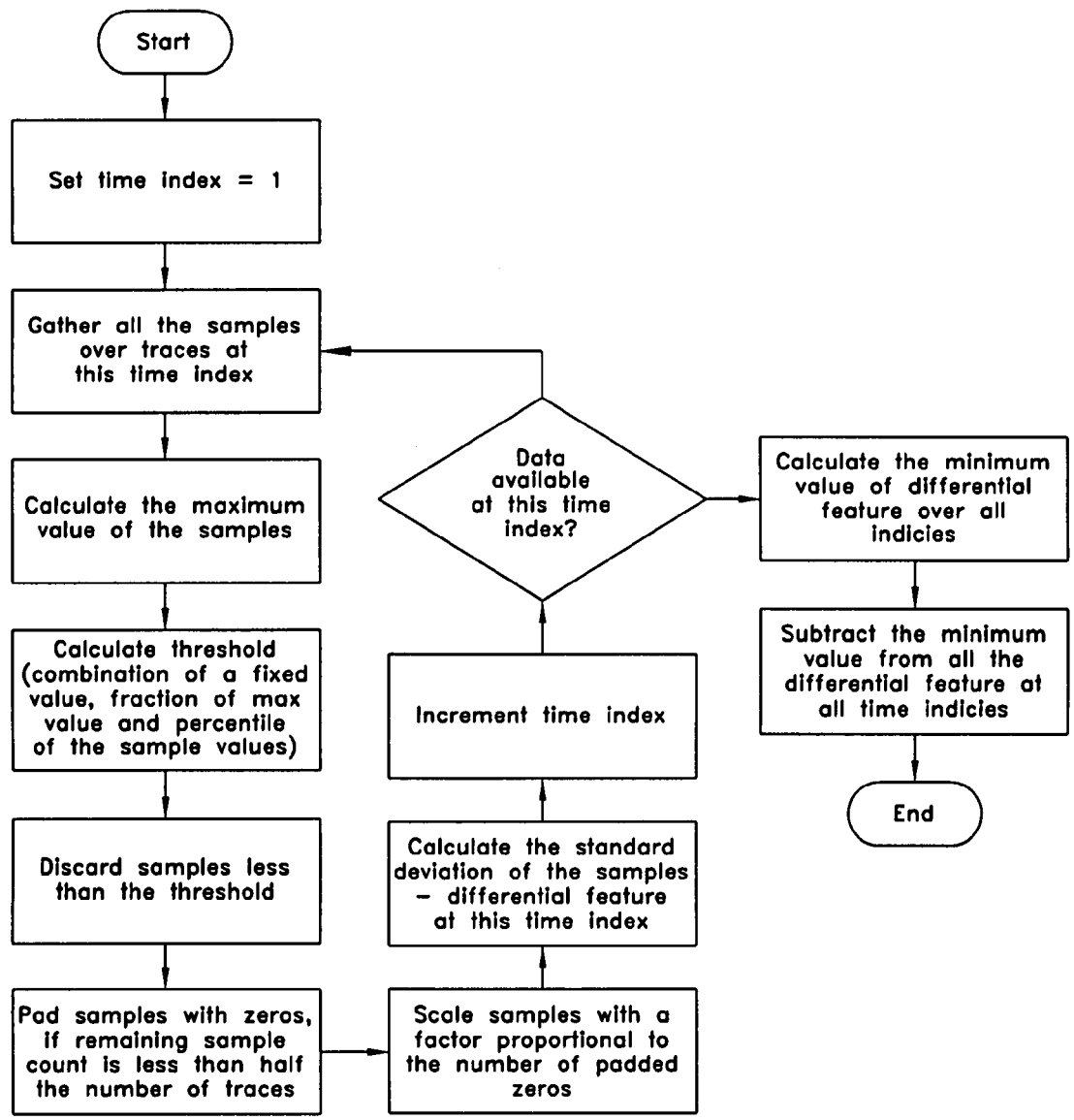
FIG. 8 illustrates the preferred steps involved in calculating the differential feature component.

The DF component is calculated for every time instant by calculating the measure of variation of all samples in all of the traces at that time instant. This is preferably done by using the following methodology which is preferably repeated for every time instant. FIG. 8 illustrates this methodology.

1. Gather all trace samples at a given time instant.
2. Calculate the maximum absolute value of all of these samples.
3. Fix a threshold that is a fraction of the maximum absolute value. The fraction is set so as to exclude samples in traces that do not have F-waves at that time instant. The fraction is preferably calculated using a late wave signal-to-noise ratio.
4. Discard all samples which are below the aforementioned threshold, since these samples are considered to contain no late-waves.
5. If the number of remaining samples is less than a predetermined count threshold (e.g., 50% of the total number of traces), pad the samples with zero to make the count equal to the count threshold and scale the samples. The scaling is proportional to the number of padded zeros. This scaling is done to prevent an artificially low variation estimate when only few of the traces have late waves at that time instant.

6. Calculate the variation estimate (standard deviation of the samples is used in the preferred embodiment) for the collection of samples. Information and entropy metrics can also be used.

After the variation estimate has been calculated for all time instants, the minimum value of the estimate is subtracted from all of the time instants. This minimum value represents the noise floor. The noise floor-corrected variation estimate values are squared and smoothed by a low-pass filter (e.g., a boxcar filter is used in the preferred embodiment). The cut-off frequency of this filter is preferably about 500 Hz, resulting in a smoothing window of about 2 ms. The filter output is square-rooted to get the differential feature estimate.

3. Differential Feature Segmentation

3a. Detection of Differential Qualifying Samples

The DF estimate is transformed into a Boolean sequence of ones and zeros by comparing the DF estimate against a certain threshold. Those time samples which have a Boolean DF sequence value of one are called the qualifying samples. The aforementioned threshold is preferably calculated as a combination of (i) a fixed value, (ii) a fraction of the maximum value of the DF estimate, and (iii) a percentile value of the DF estimate.

3b. Dilation, Erosion and Segmentation of Qualifying Samples

Dilation is done to fill the gap between two groups of qualifying samples which have a very narrow gap between them, and erosion is done to discard very narrow isolated groups of qualifying samples. Dilation prevents fragmentation of a late wave interval, and erosion discards narrow groups of qualifying samples which may constitute signal artifacts.

Dilation is a morphological filtering operation using a moving window centered at the current time sample. The output value of the current time instant is set to one if any of the input samples within the window is one. Therefore, with the dilation operation, a non-qualifying input sample with a value of zero between two close intervals of qualifying contiguous input samples will have an output value of one. The dilation operation will also extend the length of contiguous groups of qualifying samples at both ends.

Erosion is also a morphological filtering operation using a moving window centered at the current input sample. The value of the current output sample is set to zero if any of the input samples within the window is zero. Thus, the erosion operation corrects the elongation of the qualifying groups of contiguous samples caused by dilation and also discards groups of qualifying contiguous samples which are shorter than the window length. But gaps filled by dilation will not be affected by the erosion operation.

Figure 9:
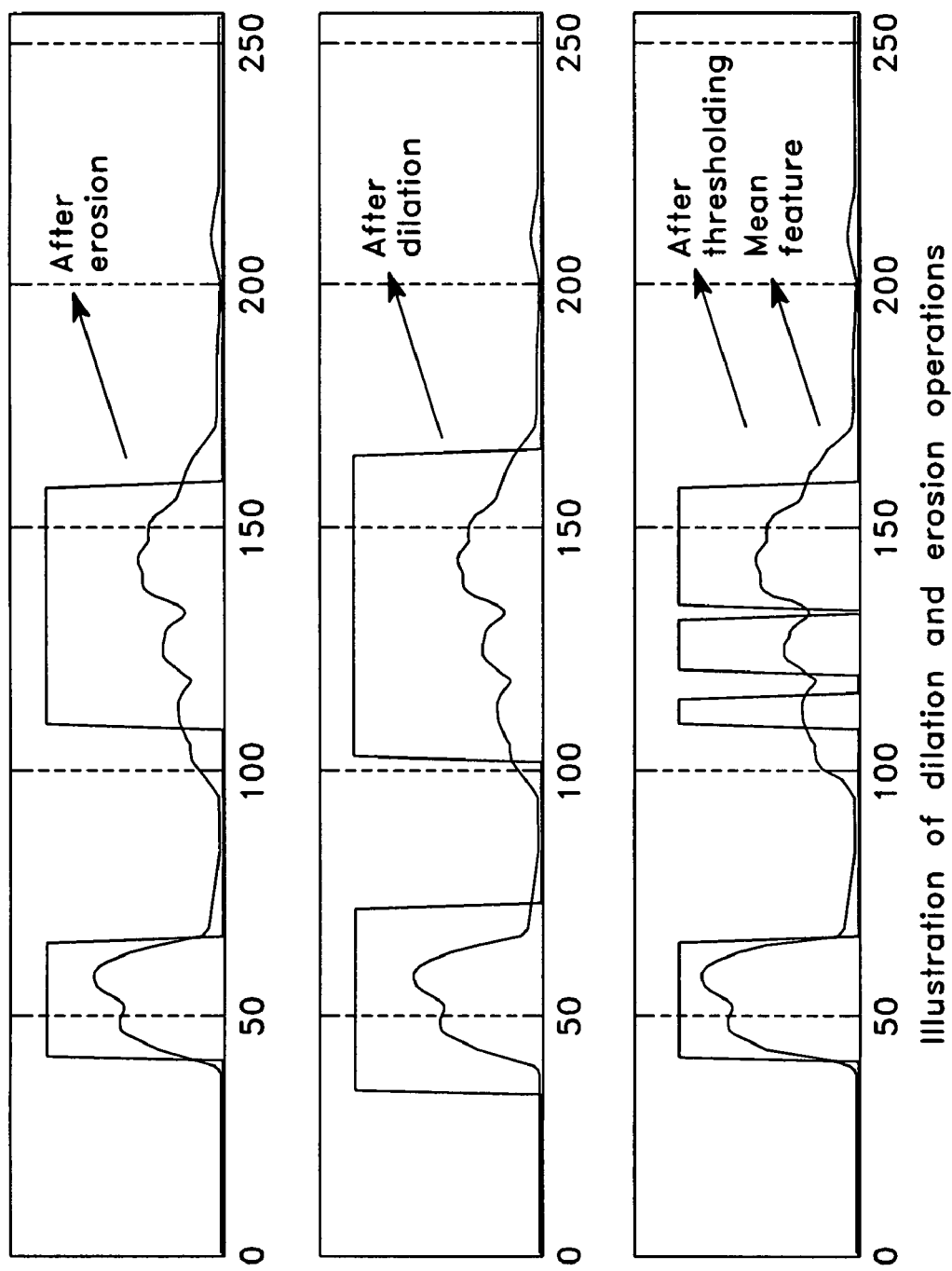
FIG. 9 illustrates dilation and erosion operations.

The preferred embodiment uses a window length of 4 ms for dilation and erosion operations. The window length is based on the shortest possible F-wave feature and the minimum quiet interval duration between two separate F-wave intervals. FIG. 9 illustrates the dilation and erosion operations.

All contiguous groups of qualifying time samples are identified. Theses contiguous groups are the late wave segments characterized using the differential feature (DF) component. These time segments will later be classified as F-wave, A-wave or Repeater segments.

4. Mean Feature Extraction

The mean feature (MF) component represents constancy across the ensemble of traces at every sample time. Samples corresponding to A-waves will have a high MF, while samples corresponding to F-waves will have a lower value. This is illustrated in FIG. 4. Any metric that measures constancy over an indexed collection of numbers can be used in this method. In a preferred embodiment of the invention, the arithmetic mean of the trace values is used as the measure of constancy. The MF component is smoothed so as to eliminate narrow breaks in the MF component and to discard narrow intervals of activity. The MF component is split into intervals of high and low activity. In accordance with the present invention, the intervals of high MF activity are considered to be late wave segments.

4a. Mean Feature Calculation and Smoothing

The MF component is calculated for every time instant by calculating a measure of constancy of all of the samples in all of the traces at that time instant. In the preferred embodiment, the arithmetic mean is used as the constancy metric.

After the constancy estimate (MF) has been calculated for all time instants, the minimum value of the constancy estimate is subtracted from all time instants. This minimum value represents the noise floor. The noise floor-corrected constancy estimate values are squared and smoothed by a low-pass filter (a boxcar filter is used in the preferred embodiment). The cut-off frequency of this filter is about 500 Hz, resulting in a smoothing window of about 2 ms. The filter output is square-rooted to get the mean feature (MF) estimate.

5. Mean Feature Segmentation

5a. Detection of Mean Qualifying Samples

The MF estimate is transformed into a Boolean sequence of ones and zeros by comparing the MF estimate against a certain threshold. Those samples which have a Boolean MF sequence value of one are called the qualifying samples. The aforementioned threshold is preferably calculated as a combination of (i) a fixed value, (ii) a fraction of the maximum value of the MF estimate, and (iii) a percentile value of the MF estimates.

5b. Dilation, Erosion and Segmentation of Qualifying Samples

As part of the mean feature (MF) segmentation process, dilation and erosion operations are performed on the qualifying MF samples. This is done in a manner that is analogous to the dilation and erosion operations discussed above in connection with the calculation of the differential feature (DF) segmentation.

All contiguous groups of qualifying samples are identified. These contiguous groups are considered to be the late wave segments characterized using the mean feature (MF) component. These segments will later be classified as A-wave or Repeater segments. Those segments that are not classified will be discarded.

6. Trace Clustering In Segments

In segments calculated from the differential feature (DF) component and mean feature (MF) component, the portions of the traces within that segment ("sub-traces") are grouped into clusters based on their morphological similarity. This is done using a similarity metric. The cluster sizes, and the time synchronization of peaks in the sub-traces within the clusters, are used to classify segments into F-wave, A-wave or Repeater segments.

In accordance with the present invention, a segment with a large cluster, and with synchronous peaks in sub-traces within the cluster will, be classified as an A-wave segment.

6a. Similarity Measure

In a preferred embodiment of the invention, the similarity metric is a modified correlation coefficient (modified CC) which compares between two sub-traces, limited to the segment interval.

The classical correlation coefficient (classical CC) is invariant to amplitude scaling of one of the traces and is defined as $$\frac{(\langle x^t y \rangle)}{\left(\sqrt{\langle x^t x \rangle \langle y^t y \rangle}\right)}.$$

where x(n) and y(n) are a pair of sub-traces in the cluster. A-wave features have the same amplitude and morphology across traces. Therefore, the classical CC is modified to reflect differences in amplitude. The modified CC is $$\frac{(\langle x^t y \rangle)}{\max(\langle x^t x \rangle \langle y^t y \rangle)}.$$

The modified CC will have a lower value if the morphology is identical and amplitudes are different.

The modified CC is calculated between two sub-traces for a number of time shifts between the two traces. The largest modified CC among the time shifts is chosen as the similarity metric.

A matrix of similarity metrics is built and this will be a symmetric matrix. The (i, j) entry in the matrix will be the similarity metric between the $i^{th}$ and $j^{th}$ traces. This matrix is called the similarity matrix.

Likewise, a matrix of time shifts at which the modified CC is maximum is also built. In this matrix, M(i, j)=−M(j, i). This matrix of time shifts is called the similarity shift matrix.

A similarity matrix and a similarity shift matrix is calculated for each segment.

6b. Cluster Formation

Clustering is done for sub-traces within each sub-segment. For each segment, the following procedure is repeated until no more sub-traces are available for clustering.

1. For each sub-trace (among the remaining sub-traces), collect other sub-traces which have a similarity metric greater than a certain threshold (the preferred embodiment uses a threshold value of 0.95) so as to create a family of similar traces. Choose the largest family of similar traces as the next cluster. If multiple families have the same number of similar traces, choose the family that has the highest similarity metric between a pair of its members. If no similar families are available, no cluster is formed.

2. Clustering ends when no more sub-traces are available or when no family of similar traces is available.

Small clusters having members less than a certain threshold (the preferred embodiment uses a threshold value of 3) are discarded.

7. Segment Classification

7a. Cluster Metrics

For each segment, three metrics are calculated. All three metrics will be high for an eventual A-wave segment and low for an F-wave segment.

1. Cluster Count Metric: Normally, A-wave segments will have one or two large clusters and the F-waves segments will have many small clusters. The cluster count metric is $$\left(\frac{1}{1 + K_1(numberOfClusters - 1)}\right).$$

The value of $K_1$ is chosen so as to provide relative weighting between the three metrics. In the preferred embodiment, $K_1$ is 0.3.

2. Cluster Shift Index Metric: Normally, in A-wave segments, traces will have a low similarity shift index. The average of the absolute values of the similarity shift index between all pairs of sub-traces in a cluster is calculated. The metric is $$\left(\frac{1}{1 + K_2(AverageShiftIndex)}\right).$$

The value of $K_2$ is chosen so as to provide relative weighting between the three metrics. In the preferred embodiment, $K_2$ is 0.2.

3. Synchronous Peak Metric: This metric has a value of zero or one. A union of all peaks in the sub-traces in a cluster is collected. For each of these peaks, a count is made of the sub-traces (peak frequency count) in which that peak is present. The synchronous peak metric is one if for any peak:
    a. The peak frequency count is higher than a certain threshold. The aforementioned threshold is a fraction of the total number of traces in the ensemble. In a preferred embodiment, the fraction is 0.5
    b. Peak amplitudes are very similar. Similarity is defined as $$\left(\frac{\max(peakAmp) - \min(peakAmp)}{\text{mean}(abs(peakAmp))}\right) < threshold.$$

The threshold for the preferred embodiment is 0.5.

7b. Cluster Classification

The three metrics are combined so as to produce an overall metric.

The segment is classified as an A-wave cluster if the overall metric exceeds a certain threshold (the preferred embodiment has a threshold value of 0.8).

The segments that are derived from the DF component and not classified as A-wave segments are classified as F-wave segments.

The segments that are derived from the MF component and not classified as A-wave segments are discarded.

8. F-Wave Latency Estimate

The F-wave latency is the onset time of the F-wave following a quiet interval. The search for the onset time is limited to an interval that includes the F-wave segment.

8a. F-Wave Latency Using Trace-By-Trace Search

F-wave latency is assigned by searching each F-wave segment in every trace for an onset following a quiet interval. When multiple F-wave segments are present, multiple F-wave latencies might be identified in the same trace.

8b. F-Wave Latency Using Differential Feature

A-waves can mask the onset of F-waves, and therefore the onset time of F-waves cannot be reliably determined by traditional methods that identify the start of activity in individual traces after a quiet interval. However, it has now been recognized that the DF component is not significantly affected by the presence of A-waves and is primarily determined by F-waves. Therefore, in accordance with the present invention, the onset of the DF component in a segment will be used as an alternate estimate of the F-wave latency for the entire ensemble of F-waves in that segment.

Figure 10:
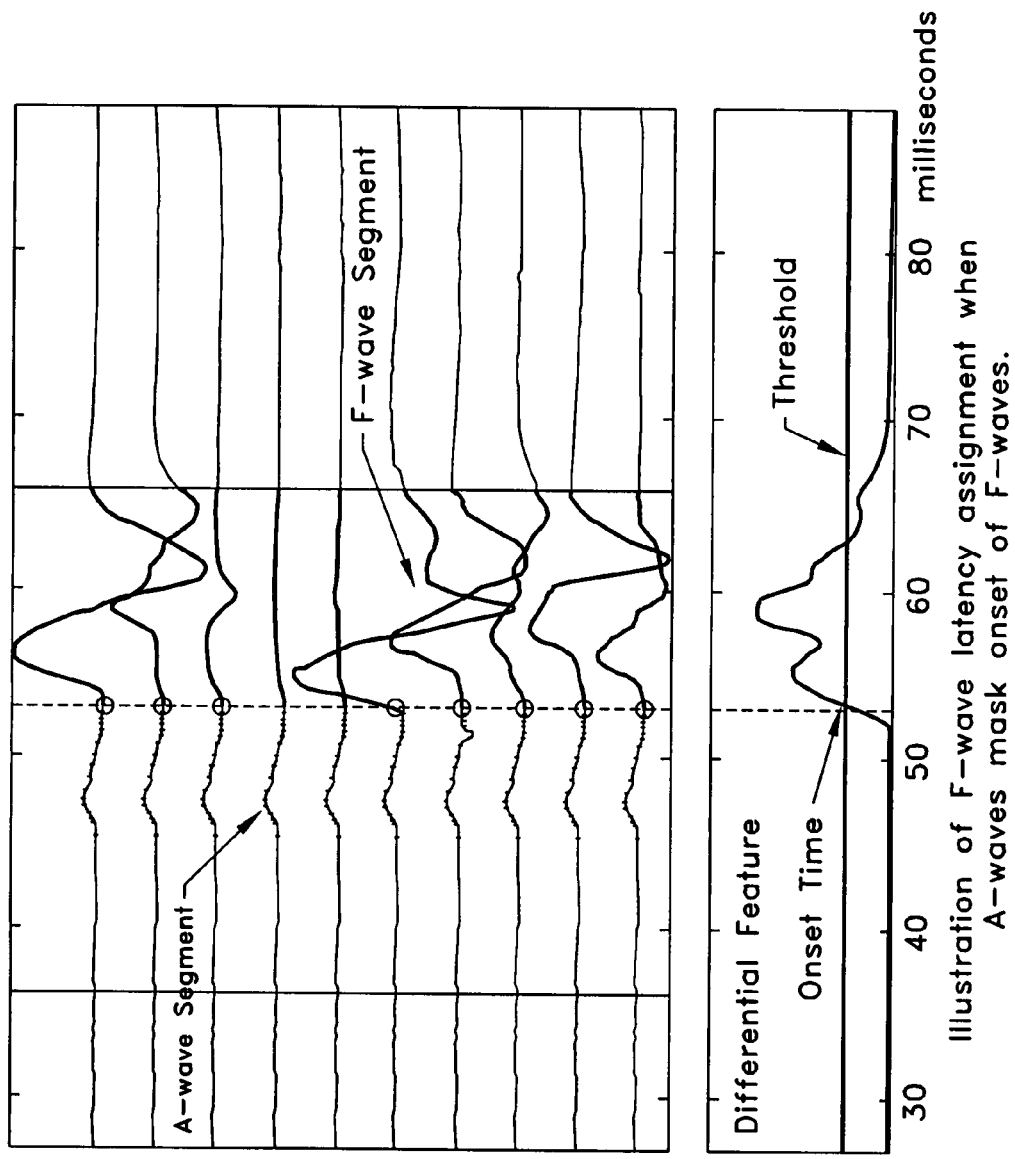
FIG. 10 illustrates the preferred approach for effecting F-wave latency assignment when A-waves mask the onset of F-waves.

The maximum value of the DF component within the segment is calculated. Referring now to FIG. 10, a threshold is set so as to be a fraction of the maximum value of the DF component. In a preferred embodiment of the invention, this fraction is in the range 0.1-0.4, depending on the typical nerve signal amplitude and noise. The threshold can also be a function of (i) the MF component prior to the F-wave segment and (ii) the DF activity within the segment. The earliest time at which the DF component exceeds the threshold is the estimated F-wave latency.

The threshold can be chosen such that the estimate provided by this method will mimic the minimum or mean F-wave latency provided by traditional methods. The threshold can be tuned by applying this technique to F-wave segments without A-wave overlap and minimizing the difference between the DF-based estimate and the mean (or minimum) F-wave latency estimate from traditional methods.

8c. Application of the F-Wave Onset Latency

Once the F-wave onset latency has been determined, the F-wave onset latency may then be used in ways well known in the art to assess neuromuscular function.

9. Implementation

The aforementioned steps are preferably performed using a general purpose computer provided with appropriate programming, or with a dedicated computer provided with appropriate programming, in a manner which will be apparent to those skilled in the art in view of the present disclosure.

Figure 12:
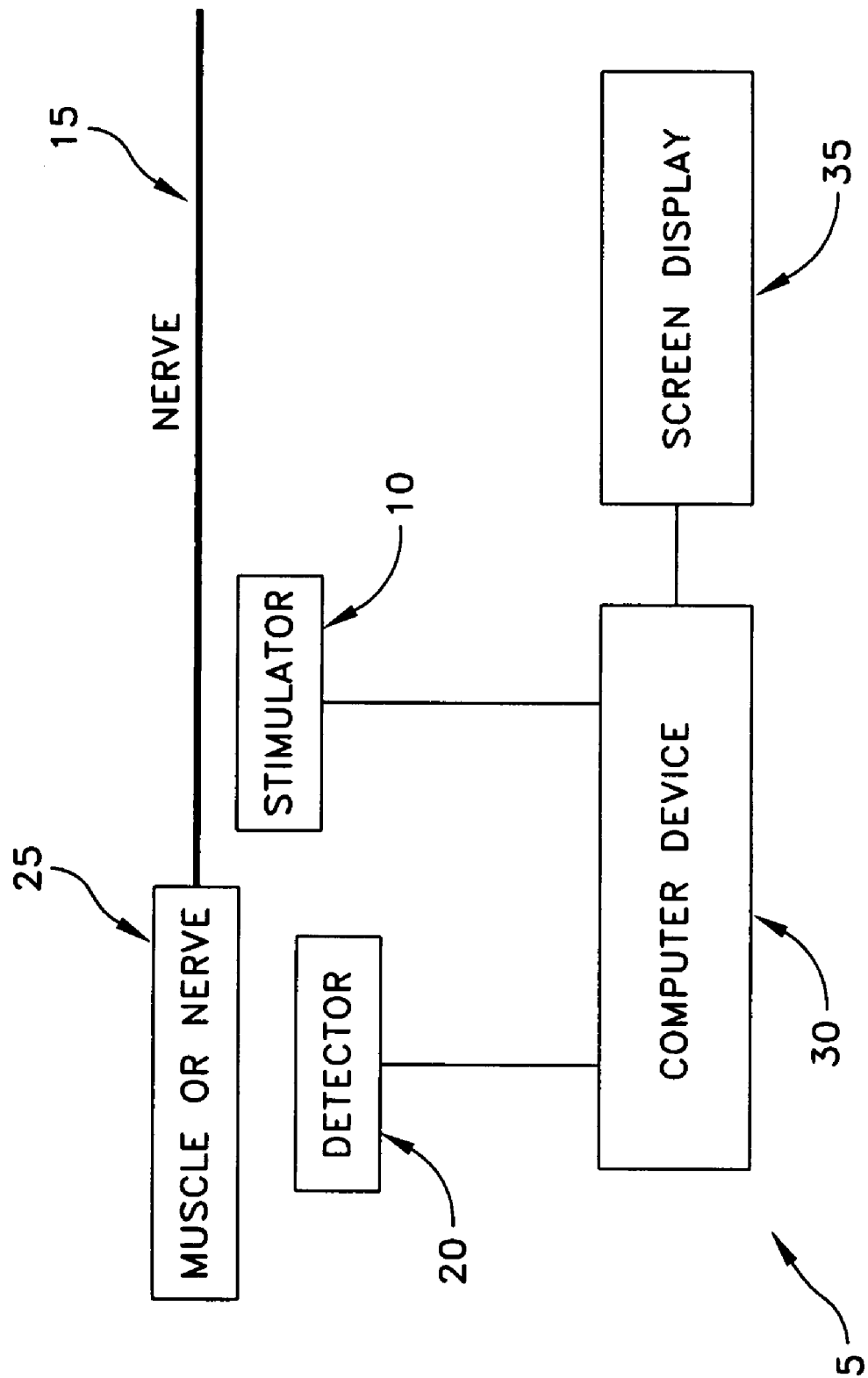
FIG. 12 is a schematic illustration of an NCS system incorporating the present invention.

By way of example but not limitation, and looking now at FIG. 12, there is shown an NCS system 5 implementing the present invention. NCS system 5 generally comprises a stimulator 10 for applying an electrical stimulus to a nerve 15 of a patient, a detector 20 for detecting the resulting electrical response of a corresponding muscle or nerve 25, and a computer device 30 for operating stimulator 10 and detector 20, and for processing the information from detector 20 in accordance with the present invention so as to determine F-wave onset latency. Computer device 30 may output its results on screen display 35.

MODIFICATIONS OF THE PREFERRED EMBODIMENT

It will be understood that many changes in the details, materials, steps and arrangements of parts, which have been herein described and illustrated in order to explain the nature of the invention, may be made by those skilled in the art without departing from the principles and scope of the present invention.

What is claimed is:

1. A method for detecting and classifying neuromuscular late wave activity so as to assess neuromuscular function in a patient, the method comprising:
   (i) electrically stimulating a nerve;
   (ii) measuring the electrical responses of the muscle innervated by the stimulated nerve, and recording the responses as an ensemble of traces;
   (iii) pre-processing, using a computer, an ensemble of traces so as to attenuate at least one of noise, power-line frequency interference (PFI) and baseline disturbances;
   (iv) identifying, using the computer, time segments of late wave activity in the ensemble of traces, wherein identifying time segments of late wave activity in the ensemble of traces comprises calculating a differential feature component and a mean feature component at every time point along the ensemble of traces and comparing the differential feature component and the mean feature component against thresholds so as to identify time segments of late wave activity in the ensemble of traces;
   (v) classifying, using the computer, the time segments of late wave activity into F-wave, A-wave and Repeater wave segments by exploiting the variable morphology of F-waves across the traces in the ensemble of traces and the fixed morphology of A-waves and Repeater waves across the traces in the ensemble of traces;
   (vi) searching, using the computer, the traces in the vicinity of the F-wave trace segments on a trace-by-trace basis so as to identify the F-wave onset latency; and
   (vii) using the identified F-wave onset latency to assess neuromuscular function in the patient.

2. A method according to claim 1 wherein the F-wave latency is determined using the ensemble of traces when the A-wave segments mask the onset of the F-waves.

3. A method according to claim 1 wherein the step of pre-processing an ensemble of traces so as to attenuate at least one of noise, power-line interference (PFI) and baseline disturbances comprises:
   a. reducing electronic noise by eliminating high frequencies on a trace-by-trace basis;
   b. estimating the amplitude and the phase of the power-line interference (PFI) components, at power-line frequency and harmonics of the power-line frequency, by a least squares estimation, and then using the estimated parameters to model the power-line interference (PFI) and thereafter remove the power-line interference (PFI) from the trace by subtracting the modeled power-line interference (PFI) from the trace; and
   c. calculating a sample-by-sample median trace from all the traces in the ensemble, and then modeling the baseline disturbance using a polynomial fit of the median trace.

4. A method according to claim 3 wherein a fixed fraction of samples are rejected, and then the polynomial fit is repeated with a reduced number of samples, in order to reduce the effect of late waves on the polynomial fit.

5. A method according to claim 4 wherein the rejected samples are those where the error between the median trace and the model is high.

6. A method according to claim 4 wherein the rejected samples are caused by late wave components in the trace, and thus their removal improves the fit of the polynomial model to the baseline disturbance.

7. A method according to claim 3 wherein the polynomial fit is accomplished using a single polynomial.

8. A method according to claim 3 wherein the polynomial fit is accomplished using piecewise continuous polynomials.

9. A method according to claim 3 wherein a weighting function is used in order to reduce the effect of late waves on the polynomial fit.

10. A method according to claim 1 wherein the differential feature component represents variability across the ensemble of traces at every sample time.

11. A method according to claim 1 wherein high values of the differential feature component are classified as F-waves.

12. A method according to claim 11 wherein standard deviation of the trace values is used as the measure of variability.

13. A method according to claim 1 wherein the mean feature component represents constancy across the ensemble of traces at every sample time.

14. A method according to claim 1 wherein high values of the mean feature component are classified as A-waves or Repeater waves.

15. A method according to claim 14 wherein the average of the trace values is used as the measure of constancy.

16. A method according to claim 1 wherein the step of classifying the time segments of late wave activity into F-wave, A-wave and Repeater segments by exploiting the variable morphology of F-waves across traces in the ensemble of traces and the fixed morphology of A-waves and Repeater waves across traces in the ensemble of traces comprises:
    grouping the waveforms within a high activity interval into clusters based on a morphology similarity metric.

17. A method according to claim 16 wherein the morphology similarity metric is the cross-correlation coefficient.

18. A method according to claim 17 wherein the interval is classified as an A-wave segment or a Repeater wave segment if the cluster size exceeds appropriate threshold levels.

19. A method according to claim 18 wherein high activity intervals of the differential feature component that are not classified as an A-wave segment or as a Repeater wave segment are classified as F-wave segments.

20. A method according to claim 18 wherein high activity intervals of the mean feature component that are not classified as an A-wave segment or as a Repeater wave segment are discarded.

21. A method according to claim 1 wherein the step of searching the traces in the vicinity of the F-wave trace segments on a trace-by-trace basis so as to identify the F-wave onset latency comprises:
    using the differential feature component to differentiate A-waves, which have lower differential feature values, from F-waves, which have higher differential feature values.

22. A method according to claim 21 wherein, after the F-wave segments have been identified, an algorithm for calculating the F-wave latency is applied to a small interval around the identified F-wave segment for each trace in the ensemble of traces; and further wherein, when an A-wave overlaps with the F-wave so that the F-wave onset is masked by an A-wave segment, the F-wave latency is established at the point at which the differential feature component drops below a certain threshold value.

23. A method according to claim 22 wherein the threshold value is established at the point at which only A-waves are present.

24. A method according to claim 1 comprising multiple F-wave latency assignments on the same trace.

25. A method for detecting and classifying neuromuscular late wave activity so as to assess neuromuscular function in a patient, the method comprising:
    electrically stimulating a nerve;
    measuring the electrical responses of the muscle innervated by the stimulated nerve, and recording the responses as an ensemble of traces;
    identifying, using a computer, time segments in an ensemble of traces, wherein identifying time segments in an ensemble of traces comprises calculating a differential feature component and a mean feature component at every time point along the ensemble of traces and comparing the differential feature component and the mean feature component against thresholds so as to identify time segments in the ensemble of traces;
    classifying, using the computer, the time segments in the ensemble of traces as quiet, A-wave, Repeater wave and/or F-wave segments;
    determining, using the computer, F-wave latency by (i) identifying any masking of an F-wave by an A-wave segment, (ii) where masking occurs, using the differential feature component to differentiate the A-wave from the F-wave and (iii) establishing the F-wave latency from the point at which only the A-wave is present; and
    using the F-wave latency to assess neuromuscular function in the patient.

26. A method according to claim 25 wherein the determination of F-wave latency is limited to a time interval around the F-wave time segments.

27. A method for detecting and classifying neuromuscular late wave activity so as to assess neuromuscular function in a patient, the method comprising:
    electrically stimulating a nerve;
    measuring the electrical responses of the muscle innervated by the stimulated nerve, and recording the responses as an ensemble of traces;
    determining, using a computer, a differential feature component and a mean feature component at every time point across an ensemble of traces;
    comparing, using the computer, the differential feature component and the mean feature component against thresholds so as to identify time segments in the ensemble of traces;
    classifying, using the computer, the identified time segments in the ensemble of traces as quiet, A-wave, Repeater wave and/or F-wave segments;
    determining, using the computer, F-wave latency by using the start of the F-wave segment to identify the onset of the F-wave; and
    using the F-wave latency to assess neuromuscular function in the patient.

* * * * *